United States Patent
deLong et al.

(10) Patent No.: US 9,877,908 B2
(45) Date of Patent: *Jan. 30, 2018

(54) COSMETIC AND PHARMACEUTICAL COMPOSITIONS AND METHODS USING 2-DECARBOXY-2-PHOSPHINICO DERIVATIVES

(71) Applicant: Duke University, Durham, NC (US)

(72) Inventors: Mitchell A. deLong, Chapel Hill, NC (US); John M. McIver, Cinccinnati, OH (US); Robert S. Youngquist, Mason, OH (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,485

(22) Filed: May 5, 2017

(65) Prior Publication Data

US 2017/0239160 A1    Aug. 24, 2017

Related U.S. Application Data

(60) Division of application No. 15/099,362, filed on Apr. 14, 2016, now Pat. No. 9,675,539, which is a continuation of application No. 14/099,756, filed on Dec. 6, 2013, now Pat. No. 9,346,837, which is a continuation of application No. 11/476,246, filed on Jun. 28, 2006, now abandoned, which is a division of application No. 09/774,558, filed on Jan. 13, 2001, now abandoned.

(60) Provisional application No. 60/193,845, filed on Mar. 31, 2000.

(51) Int. Cl.
A61K 8/55 (2006.01)
A61Q 1/10 (2006.01)
A61Q 7/00 (2006.01)

(52) U.S. Cl.
CPC .................. A61K 8/55 (2013.01); A61Q 1/10 (2013.01); A61Q 7/00 (2013.01)

(58) Field of Classification Search
CPC .......... A61K 31/662; A61Q 5/00; A61Q 7/00; A61Q 9/00; A61Q 19/00
See application file for complete search history.

(56) References Cited

U.S. PATENT DOCUMENTS

| | | | | |
|---|---|---|---|---|
| 5,508,303 A * | 4/1996 | Isogaya | ................ | A61K 8/4973 514/468 |
| 6,262,105 B1 * | 7/2001 | Johnstone | .............. | A61K 8/365 514/430 |
| 6,894,175 B1 * | 5/2005 | DeLong | ............ | C07C 405/0008 549/222 |
| 7,074,942 B2 * | 7/2006 | deLong | ............ | C07C 405/0008 549/222 |
| 7,115,659 B2 * | 10/2006 | DeLong | ............ | C07C 405/0008 514/463 |
| 9,346,837 B2 * | 5/2016 | deLong | ................... | A61K 8/55 |

* cited by examiner

*Primary Examiner* — Lakshmi S Channavajjala
(74) *Attorney, Agent, or Firm* — Michael Best & Friedrich LLP

(57) ABSTRACT

A method for treating hair loss in mammals uses compositions containing 2-decarboxy-2-phosphinico prostaglandin derivatives. The compositions can be applied topically to the skin. The compositions can arrest hair loss, reverse hair loss, and promote hair growth. Compositions containing 2-decarboxy-2-phosphinico prostaglandin derivatives can also be used to lower intraocular pressure and treat bone disorders.

17 Claims, No Drawings

COSMETIC AND PHARMACEUTICAL COMPOSITIONS AND METHODS USING 2-DECARBOXY-2-PHOSPHINICO DERIVATIVES

CROSS-REFERENCE TO RELATED APPLICATIONS

This patent application is a divisional of U.S. patent application Ser. No. 15/099,362, filed on Apr. 14, 2016, which is a continuation of U.S. patent application Ser. No. 14/099,756, filed on Dec. 6, 2013, issued as U.S. Pat. No. 9,346,837, on May 24, 2016, which is a continuation of U.S. patent application Ser. No. 11/476,246, filed Jun. 28, 2006, which is a divisional of U.S. patent application Ser. No. 09/774,558, filed Jan. 31, 2001, which claims priority to U.S. Provisional Patent Application No. 60/193,845, filed Mar. 31, 2000, the contents of all of which are hereby incorporated by reference. Priority to these applications is hereby claimed.

FIELD OF THE INVENTION

This invention relates to compositions and methods for using 2-decarboxy-2-phosphinico derivatives of prostaglandins. More particularly, this invention relates to the use of 2-decarboxy-2-phosphinico derivatives of prostaglandins for treating hair loss in mammals. This invention further relates to the use of 2-decarboxy-2-phosphinico derivatives of prostaglandins for lowering intraocular pressure and treating bone disorders in mammals.

BACKGROUND OF THE INVENTION

Hair Loss—Cosmetic Treatment

Hair loss is a common problem which is, for example, naturally occurring or chemically promoted through the use of certain therapeutic drugs designed to alleviate conditions such as cancer. Often such hair loss is accompanied by lack of hair re-growth which causes partial or full baldness.

Hair growth on the scalp does not occur continuously, but rather occurs by a cycle of activity involving alternating periods of growth and rest. This cycle is divided into three main stages; anagen, catagen, and telogen. Anagen is the growth phase of the cycle and is characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth ceases. The next phase, telogen, is characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. When hair growth ceases, most of the hair follicles reside in telogen and anagen is not engaged, thus causing the onset of full or partial baldness.

Attempts to invoke the re-growth of hair have been made by, for example, the promotion or prolongation of anagen. Currently, there are two drugs approved by the United States Food and Drug Administration for the treatment of male pattern baldness: topical minoxidil (marketed as ROGAINE® by Pharmacia & Upjohn), and oral finasteride (marketed as PROPECIA® by Merck & Co., Inc.). However, the search for efficacious hair growth inducers is ongoing due to factors including safety concerns and limited efficacy.

The thyroid hormone thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. See, e.g., Berman, "Peripheral Effects of L-Thyroxine on Hair Growth and Coloration in Cattle", *Journal of Endocrinology*, Vol. 20, pp. 282-292, (1960); and Gunaratnam, "The Effects of Thyroxine on Hair Growth in the Dog", *J. Small Anim. Pract.*, Vol. 27, pp. 17-29 (1986). Furthermore, T3 and T4 have been the subject of several patent publications relating to treatment of hair loss. See, e.g., Fischer et al., DE 1,617,477, published Jan. 8, 1970; Mortimer, GB 2,138,286, published Oct. 24, 1984; and Lindenbaum, WO 96/25943, assigned to Life Medical Sciences, Inc., published Aug. 29, 1996.

Unfortunately, however, administration of T3 or T4, or both, to treat hair loss is often not practicable because these thyroid hormones can induce significant cardiotoxicity. See, e.g., Walker et al., U.S. Pat. No. 5,284,971, assigned to Syntex, issued Feb. 8, 1994 and Emmett et al., U.S. Pat. No. 5,061,798, assigned to Smith Kline & French Laboratories, issued Oct. 29, 1991.

In an alternative approach, prostaglandins have been proposed to promote hair growth because prostaglandins may have a similar benefit to thyroid hormones, i.e., increasing hair length and changing pigmentation. Naturally occurring prostaglandins (e.g., $PGA_2$, $PGB_2$, $PGE_1$, $PGF_{2\alpha}$, and $PGI_2$) are C-20 unsaturated fatty acids. $PGF_{2\alpha}$, the naturally occurring Prostaglandin F analog in humans, is characterized by hydroxyl groups at the C9 and C11 positions on the alicyclic ring, a cis-double bond between C5 and C6, and a trans-double bond between C13 and C14. $PGF_{2\alpha}$ has the formula:

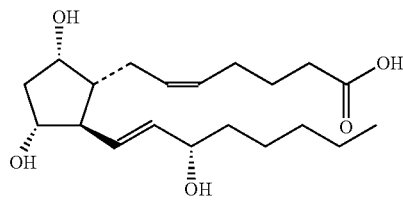 [SMILES: CCCCC[C@H](O)/C=C/[C@@H]1[C@@H](C/C=C\CCCC(=O)O)[C@@H](O)C[C@H]1O]

Analogs of naturally occurring Prostaglandin F are known in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.*, Vol. 93, pp. 1533-1564 (1993); G. L. Bundy and F. H. Lincoln, "Synthesis of 17-Phenyl-18,19,20-Trinorprostaglandins: I. The $PG_1$ Series", *Prostaglandin*, Vol. 9, No. 1, pp. 1-4 (1975); W. Bartman, G. Beck, U. Lerch, H. Teufel, and B. Scholkens, "Luteolytic Prostaglandin: Synthesis and Biological Activity", *Prostaglandin*, Vol. 17, No. 2, pp. 301-311 (1979).

Prostaglandins in general have a wide range of biological activities. For example, $PGE_2$ has the following properties: a) regulator of cell proliferation, b) regulator of cytokine synthesis, c) regulator of immune responses and d) inducer of vasodilatation. Vasodilatation is thought to be one of the mechanisms of how minoxidil provides a hair growth benefit. In vitro results in the literature also indicate some anti-inflammatory properties of the prostaglandins. c.f.; Tanaka, H., *Br J. Pharm.*, 116, 2298, (1995).

However, previous attempts at using prostaglandins to promote hair growth have been unsuccessful. Different prostaglandins can bind to multiple receptors at various concentrations with a biphasic effect. Therefore, it is an object of this invention to provide methods for using prostaglandins to grow hair and to provide compositions that promote hair growth. It is a further object of this invention to provide a selection of appropriate prostaglandins that will promote hair growth in humans and lower animals.

Bone Disorders—Pharmaceutical Treatment

In addition to the biological activities discussed above, prostaglandins are also known to affect bone. Therefore, it is a further object of this invention to provide compositions and methods for using prostaglandins to treat bone disorders.

Accelerated bone loss may result from drug administration, such as corticosteroids, prolonged bed rest, disuse of a limb, and microgravity. In osteoporotics, an imbalance in the bone remodeling process develops in which bone is resorbed at a rate faster than it is being made. Although this imbalance occurs to some extent in most individuals, male and female, as they age, it is more severe and occurs at a younger age in osteoporotics, particularly those who develop the post menopausal form of the condition. Bone loss due to the above conditions can result in complete removal of trabeculae and a deterioration of bone architecture such that the strength of the remaining bone decreases disproportionately.

To completely return the bone to normal strength, new trabeculae should be formed to restore architecture and increase bone mass. When restoration of normal architecture is associated with an increase in strength and return to normal stiffness and shock absorbing capability, the bone is less likely to fracture. Subjects suffering from other bone disorders, such as osteoarthritis, Paget's disease, periodontal disease, and fractures may also benefit from treatments that restore normal architecture and bone mass.

Various agents have been tried in attempts to treat bone disorders by slowing bone loss or increasing bone mass. Agents for slowing bone loss and reestablishing bone density are exemplified by antiresorptive agents such as bisphosphonates.

Prostaglandin E analogs are potent stimulators of bone resorption and formation. Anabolic agents such as some prostaglandin E analogs may be detrimental to one suffering from bone disorders such as osteoporosis because increased resorption may cause perforation and loss of trabeculae or may weaken the existing trabecular structure. Increased resorption may also occur in cortical bone, which may increase the incidence of fracture at some sites.

Anabolic agents such as fluoride and other prostaglandin E analogs have been used to increase bone mass. However, such agents have failed to build bone that is structurally and architecturally similar to the type of bone lost.

Naturally occurring $PGF_{2\alpha}$, shown above, is also known to affect bone resorption. However, naturally occurring prostaglandins have several drawbacks that limit their desirability for systemic administration. Naturally occurring prostaglandins are characterized by their activity at a certain prostagladin receptor, however, their activity is not limited to any one receptor. Therefore, systemic administration of naturally occurring prostaglandins can cause side effects such as inflammation, surface irritation, smooth muscle contraction, pain, and bronchoconstriction.

Therefore, it is an object of this invention to provide compositions and methods using prostaglandins to treat bone disorders without significant undesirable side effects. It is a further object of this invention to provide a selection of appropriate prostaglandins that will promote bone growth in humans and lower animals.

Intraocular Pressure—Pharmaceutical Treatment

In addition to the pharmacological properties discussed above, naturally occurring prostaglandins are also known to reduce intraocular pressure. Reduction of intraocular pressure is effective to treat disorders such as glaucoma. See C. Iiljebris, G. Selen, B. Resul, J. Sternschantz, and U. Hacksell, "Derivatives of 17-Phenyl-18, 19,20-trinorprostaglandin $F_2\alpha$. Isopropyl Ester: Potential Antiglaucoma Agents", *Journal of Medicinal Chemistry*, Vol. 38, No. 2, pp. 289-304 (1995). However, as discussed above, the naturally occurring prostaglandins generally are not specific for any one prostaglandin receptor, and thus are known to cause side effects.

Therefore, it is an object of this invention to provide compositions and methods using prostaglandins to lower intraocular pressure without significant undesirable side effects. It is a further object of this invention to provide a selection of appropriate prostaglandins that will lower intraocular pressure in humans and lower animals.

SUMMARY OF THE INVENTION

This invention relates to compositions and methods for treating hair loss. The methods comprise administering the compositions comprising specific prostaglandins that interact strongly with hair-selective receptors, such as the FP receptor. The choice of prostaglandin is important because the prostaglandin must selectively activate the FP receptor and not activate any other receptors that would negate the effect of activating the FP receptor or that would cause significant undesirable side effects. The prostaglandins used in this invention are 2-decarboxy-2-phosphinico derivatives of prostaglandins. This invention further relates to the use of 2-decarboxy-2-phosphinico derivatives of prostaglandins to prepare compositions for treating hair loss. The compositions comprise: component A) the 2-decarboxy-2-phosphinico derivative of a prostaglandin, component B) a carrier, and optionally component C) an activity enhancer.

This invention further relates to compositions and methods for treating bone disorders. The methods comprise administering, to subjects suffering from bone disorders such as osteoporosis, compositions comprising 2-decarboxy-2-phosphinico derivatives of prostaglandins. This invention further relates to the use of 2-decarboxy-2-phosphinico derivatives of prostaglandins to prepare compositions for treating bone disorders.

This invention further relates to compositions and methods for lowering intraocular pressure. The methods comprise administering, to subjects suffering from conditions such as glaucoma, compositions comprising 2-decarboxy-2-phosphinico derivatives of prostaglandins. This invention further relates to the use of 2-decarboxy-2-phosphinico derivatives of prostaglandins to prepare compositions for lowering intraocular pressure.

DETAILED DESCRIPTION OF THE INVENTION

In one aspect, this invention relates to compositions for treating hair loss in mammals. "Treating hair loss" includes arresting hair loss or reversing hair loss, or both, and promoting hair growth.

Publications and patents are referred to throughout this disclosure. All U.S. Patents cited herein are hereby incorporated by reference.

All percentages, ratios, and proportions used herein are by weight unless otherwise specified.

Definition and Usage of Terms

The following is a list of definitions for terms, as used herein:

"Activate" means binding and signal transduction of a receptor.

"Acyl group" means a monovalent group suitable for acylating a nitrogen atom to form an amide or carbamate, an alcohol to form a carbonate, or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Aromatic group" means a monovalent group having a monocyclic ring structure or fused bicyclic ring structure. Monocyclic aromatic groups contain 5 to 10 carbon atoms, preferably 5 to 7 carbon atoms, and more preferably 5 to 6 carbon atoms in the ring. Bicyclic aromatic groups contain 8 to 12 carbon atoms, preferably 9 or 10 carbon atoms in the ring. Aromatic groups are unsubstituted. The most preferred aromatic group is phenyl.

"Carbocyclic group" means a monovalent saturated or unsaturated hydrocarbon ring. Carbocyclic groups are monocyclic, or are fused, spiro, or bridged bicyclic ring systems. Monocyclic carbocyclic groups contain 4 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups are unsubstituted. Preferred carbocyclic groups include cyclopentyl, cyclohexyl, cyclohexenyl, cycloheptyl, and cyclooctyl. More preferred carbocyclic groups include cyclohexyl, cycloheptyl, and cyclooctyl. The most preferred carbocyclic group is cycloheptyl. Carbocyclic groups are not aromatic.

"Cyano group" means a group containing a nitrile functionality.

"FP agonist" means a compound that activates the FP receptor.

"FP receptor" means known human FP receptors, their splice variants, and undescribed receptors that have similar binding and activation profiles as the known human FP receptors. "FP" means the receptor is of the class which has the highest affinity for $PGF_{2\alpha}$ of all the naturally occurring prostaglandins. FP refers to a known protein.

"Halogen atom" means F, Cl, Br, or I. Preferably, the halogen atom is F, Cl, or Br; more preferably Cl or F; and most preferably F.

"Halogenated heterogenous group" means a substituted heterogenous group or a substituted heterocyclic group, wherein at least one substituent is a halogen atom. Halogenated heterogenous groups can have a straight, branched, or cyclic structure. Preferred halogenated heterogenous groups have 1 to 12 carbon atoms, more preferably 1 to 6 carbon atoms, and most preferably 1 to 3 carbon atoms. Preferred halogen atom substituents are Cl and F.

"Halogenated hydrocarbon group" means a substituted monovalent hydrocarbon group or a substituted carbocyclic group, wherein at least one substituent is a halogen atom. Halogenated hydrocarbon groups can have a straight, branched, or cyclic structure. Preferred halogenated hydrocarbon groups have 1 to 12 carbon atoms, more preferably 1 to 6 carbon atoms, and most preferably 1 to 3 carbon atoms. Preferred halogen atom substituents are Cl and F. The most preferred halogenated hydrocarbon group is trifluoromethyl.

"Heteroaromatic group" means an aromatic ring containing carbon and 1 to 4 heteroatoms in the ring. Heteroaromatic groups are monocyclic or fused bicyclic rings. Monocyclic heteroaromatic groups contain 5 to 10 member atoms (i.e., carbon and heteroatoms), preferably 5 to 7, and more preferably 5 to 6 in the ring. Bicyclic heteroaromatic rings contain 8 to 12 member atoms, preferably 9 or 10 in the ring. Heteroaromatic groups are unsubstituted. Preferred heteroaromatic groups include thienyl, thiazolyl, purinyl, pyrimidyl, pyridyl, and furanyl. More preferred heteroaromatic groups include thienyl, furanyl, and pyridyl. The most preferred heteroaromatic group is thienyl.

"Heteroatom" means an atom other than carbon in the ring of a heterocyclic group or the chain of a heterogeneous group. Preferably, heteroatoms are selected from the group consisting of nitrogen, sulfur, and oxygen atoms. Groups containing more than one heteroatom may contain different heteroatoms.

"Heterocyclic group" means a saturated or unsaturated ring structure containing carbon and 1 to 4 heteroatoms in the ring. No two heteroatoms are adjacent in the ring. Heterocyclic groups are not aromatic. Heterocyclic groups are monocyclic, or are fused or bridged bicyclic ring systems. Monocyclic heterocyclic groups contain 4 to 10 member atoms (i.e., including both carbon atoms and at least 1 heteroatom), preferably 4 to 7, and more preferably 5 to 6 in the ring. Bicyclic heterocyclic groups contain 8 to 12 member atoms, preferably 9 or 10 in the ring. Heterocyclic groups are unsubstituted. Preferred heterocyclic groups include piperzyl, morpholinyl, tetrahydrofuranyl, tetrahydropyranyl, and piperdyl.

"Heterogeneous group" means a saturated or unsaturated chain containing 1 to 18 member atoms (i.e., including both carbon and at least one heteroatom). No two heteroatoms are adjacent. Preferably, the chain contains 1 to 12 member atoms, more preferably 1 to 6, and most preferably 1 to 4. The chain may be straight or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond. Heterogeneous groups are unsubstituted.

"Monovalent hydrocarbon group" means a chain of 1 to 18 carbon atoms, preferably 1 to 12 carbon atoms. "Lower monovalent hydrocarbon group" means a monovalent hydrocarbon group having 1 to 6, preferably 1 to 4 carbon atoms. Monovalent hydrocarbon groups may have a straight chain or branched chain structure. Preferred monovalent hydrocarbon groups have one or two branches, preferably 1 branch. Preferred monovalent hydrocarbon groups are saturated. Unsaturated monovalent hydrocarbon groups have one or more double bonds, one or more triple bonds, or combinations thereof. Preferred unsaturated monovalent hydrocarbon groups have one or two double bonds or one triple bond; more preferred unsaturated monovalent hydrocarbon groups have one double bond.

"Pharmaceutically acceptable" means suitable for use in a human or other mammal.

"Prostaglandin" means a fatty acid derivative which has a variety of potent biological activities of a hormonal or regulatory nature.

"Protecting group" is a group that replaces the active hydrogen of a hydroxyl moiety thus preventing undesired side reaction at the hydroxyl moiety. Use of protecting groups in organic synthesis is well known in the art. Examples of protecting groups are found in Chapter 2 *Protecting Groups in Organic Synthesis* by Greene, T. W. and Wuts, P. G. M., $2^{nd}$ ed., Wiley & Sons, Inc., 1991. Preferred protecting groups include silyl ethers, alkoxymethyl ethers, tetrahydropyranyl, tetrahydrofuranyl, esters, and substituted or unsubstituted benzyl ethers.

"Safe and effective amount" means a quantity of a prostaglandin high enough to provide a significant positive modification of the subject's condition to be treated, but low enough to avoid serious side effects (at a reasonable benefit/risk ratio).

"Selective" means having a binding or activation preference for a specific receptor over other receptors which can be quantitated based upon receptor binding or activation assays.

"Subject" means a living vertebrate animal such as a mammal (preferably human) in need of treatment.

"Substituted aromatic group" means an aromatic group wherein 1 to 4 of the hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, aromatic groups, substituted aromatic groups, or any combination thereof. More preferred substituents include halogen atoms, monovalent hydrocarbon groups, and substituted monovalent hydrocarbon groups. Preferred substituted aromatic groups include naphthyl. The substituents may be substituted at the ortho, meta, or para position on the ring, or any combination thereof. The preferred substitution pattern on the ring is ortho or meta. The most preferred substitution pattern is ortho.

"Substituted carbocyclic group" means a carbocyclic group wherein 1 to 4 hydrogen atoms bonded to carbon atoms in the ring have been replaced with other substituents. Preferred substituents include: halogen atoms, cyano groups, monovalent hydrocarbon groups, monovalent heterogeneous groups, substituted monovalent hydrocarbon groups, aromatic groups, substituted aromatic groups, or any combination thereof. More preferred substituents include halogen atoms and substituted monovalent hydrocarbon groups. Carbocyclic group does not include aromatic rings.

"Substituted heteroaromatic group" means a heteroaromatic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, phenyl groups, phenoxy groups, or any combination thereof. More preferred substituents include halogen atoms, halogenated hydrocarbon groups, halogenated heterogenous groups, monovalent hydrocarbon groups, and phenyl groups.

"Substituted heterocyclic group" means a heterocyclic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, halogenated hydrocarbon groups, halogenated heterogenous groups, phenyl groups, phenoxy groups, or any combination thereof. More preferred substituents include halogen atoms and halogenated hydrocarbon groups. Substituted heterocyclic groups are not aromatic.

"Substituted heterogeneous group" means a heterogeneous group, wherein 1 to 4 of the hydrogen atoms bonded to carbon atoms in the chain have been replaced with other substituents. Preferred substituents include halogen atoms, hydroxy groups, alkoxy groups (e.g., methoxy, ethoxy, propoxy, butoxy, and pentoxy), aryloxy groups (e.g., phenoxy, chlorophenoxy, tolyloxy, methoxyphenoxy, benzyloxy, alkyloxycarbonylphenoxy, and acyloxyphenoxy), acyloxy groups (e.g., propionyloxy, benzoyloxy, and acetoxy), carbamoyloxy groups, carboxy groups, mercapto groups, alkylthio groups, acylthio groups, arylthio groups (e.g., phenylthio, chlorophenylthio, alkylphenylthio, alkoxyphenylthio, benzylthio, and alkyloxycarbonylphenylthio), aromatic groups (e.g., phenyl and tolyl), substituted aromatic groups (e.g., alkoxphenyl, alkoxycarbonylphenyl, and halophenyl), heterocyclic groups, heteroaromatic groups, and amino groups (e.g., amino, mono- and di-alkylamino having 1 to 3 carbon atoms, methylphenylamino, methylbenzylamino, alkanylamido groups of 1 to 3 carbon atoms, carbamamido, ureido, and guanidino).

"Substituted monovalent hydrocarbon group" means a monovalent hydrocarbon group wherein 1 to 4 of the hydrogen atoms bonded to carbon atoms in the chain have been replaced with other substituents. Preferred substituents include halogen atoms; halogenated hydrocarbon groups; halogenated heterogenous groups; alkyl groups (e.g., methyl, ethyl, propyl, and butyl); hydroxy groups; alkoxy groups (e.g., methoxy, ethoxy, propoxy, butoxy, and pentoxy); aryloxy groups (e.g., phenoxy, chlorophenoxy, tolyloxy, methoxyphenoxy, benzyloxy, alkyloxycarbonylphenoxy, and acyloxyphenoxy); acyloxy groups (e.g., propionyloxy, benzoyloxy, and acetoxy); carbamoyloxy groups; carboxy groups; mercapto groups; alkylthio groups; acylthio groups; arylthio groups (e.g., phenylthio, chlorophenylthio, alkylphenylthio, alkoxyphenylthio, benzylthio, and alkyloxycarbonylphenylthio); aryl groups (e.g., phenyl, tolyl, alkoxyphenyl, alkoxycarbonylphenyl, and halophenyl); heterocyclyl groups; heteroaryl groups; and amino groups (e.g., amino, mono- and di-alkanylamino groups of 1 to 3 carbon atoms, methylphenylamino, methylbenzylamino, alkanylamido groups of 1 to 3 carbon atoms, carbamamido, ureido, and guanidino).

Prostaglandins Used in the Invention

The prostaglandins suitable for use in this invention are selected from the group consisting of 2-decarboxy-2-phosphinico derivatives of prostaglandins; optical isomers, diastereomers, and enantiomers of the 2-decarboxy-2-phosphinico derivatives; pharmaceutically-acceptable salts of the 2-decarboxy-2-phosphinico derivatives; and biohydrolyzable amides, esters, and imides of the 2-decarboxy-2-phosphinico derivatives.

Suitable 2-decarboxy-2-phosphinico derivatives can have a formula selected from the group consisting of:

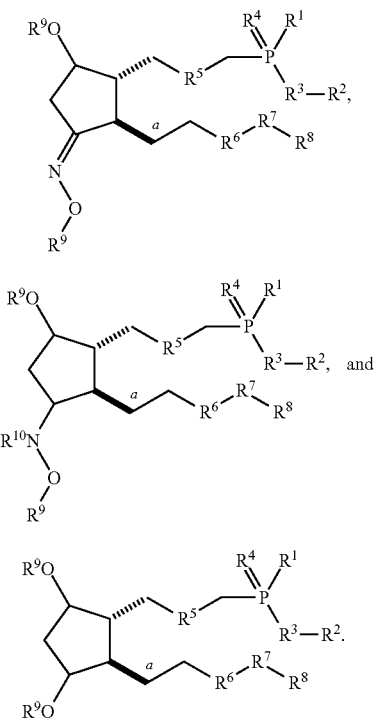

Formula I

Formula II, and

Formula III $R^1$ is selected from the group consisting of a hydrogen atom, lower monovalent hydrocarbon groups, lower substituted monovalent hydrocarbon groups, and lower heterogeneous groups. $R^1$ is preferably selected from the group consisting of a hydrogen atom; an alkyl group such as methyl, ethyl, n-propyl, isopropyl, n-butyl, isobutyl, and t-butyl; a halogenated hydrocarbon group such as trifluoromethyl or $CH_2CH_2CF_3$; $CH_2CH_2OH$, and $CH_2CH_2CH_2OH$. More preferably, $R^1$ is a hydrogen atom, methyl, ethyl, n-propyl, isopropyl, n-butyl, isobutyl, t-butyl, trifluoromethyl, $CH_2CH_2CF_3$, $CH_2CH_2OH$, or $CH_2CH_2CH_2OH$. Most preferably, $R^1$ is a hydrogen atom, methyl, ethyl, n-propyl, isopropyl, or $CH_2CH_2OH$.

$R^2$ is selected from the group consisting of a hydrogen atom, a monovalent hydrocarbon group, a substituted monovalent hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. Preferably $R^2$ is H, $CH_2CO_2H$, $CH_2C(O)NHOH$, methyl, $CF_3$, ethyl, n-propyl, isopropyl, $CH_2CH_2OH$, $CH_2CH(OH)CH_2OH$, benzyl, or t-butyl. More preferably, $R^2$ is H, methyl, $CF_3$, ethyl, n-propyl, isopropyl, $CH_2CH_2OH$, $CH_2C(O)NHOH$, and benzyl. Most preferably, $R^2$ is H, methyl, $CF_3$, ethyl, n-propyl, isopropyl, or $CH_2CH_2OH$.

$R^3$ is selected from the group consisting of an oxygen atom, a sulfur atom, and NH. Preferably, $R^3$ is an oxygen atom or NH; more preferably, $R^3$ is an oxygen atom.

$R^4$ is selected from the group consisting of an oxygen atom and a sulfur atom. Preferably, $R^4$ is an oxygen atom.

$R^5$ is a divalent group. $R^5$ is selected from the group consisting of a hydrocarbon group, a substituted hydrocarbon group, a heterogeneous group, and a substituted heterogeneous group. $R^5$ may be saturated or unsaturated, i.e., $R^5$ may contain one or more single bond, double bond, triple bond, or combinations thereof. When $R^5$ is a heterogeneous group, $R^5$ has only one heteroatom, which is selected from the group consisting of oxygen, sulfur, and nitrogen. The preferred heteroatom is oxygen. $R^5$ preferably has 1 to 5 member atoms, more preferably 3 to 5 member atoms.

Bond a is selected from the group consisting of a single bond, a trans double bond, and a triple bond.

$R^6$ is a divalent group selected from the group consisting of —C(O)— and —C($R^9$)(O$R^9$)—.

$R^7$ is selected from the group consisting of a divalent group having the formula —(C$R^9$($R^9$))$_p$—X—(C$R^9$($R^9$))$_q$, wherein p is an integer from 0 to 3 and q is an integer from 0 to 3, and wherein X is selected from the group consisting of an oxygen atom, a divalent hydrocarbon group, a sulfur atom, SO, $SO_2$, and $NR^9$. Preferably, X is selected from the group consisting of a single bond, a trans double bond, a triple bond, an oxygen atom, a sulfur atom, and $NR^9$.

$R^8$ is selected from the group consisting of a methyl group, a carbocyclic group, a substituted carbocyclic group, a heterocyclic group, a substituted heterocyclic group, aromatic group, a substituted aromatic group, a heteroaromatic group, a substituted heteroaromatic group. When $R^8$ is a monocyclic group, it has 5 to 10 member atoms. When $R^8$ is a bicyclic group, it has 8 to 12 member atoms. Preferably, $R^8$ is selected from the group consisting of a monocyclic carbocyclic group, a substituted monocyclic carbocyclic group, a monocyclic heterocyclic group, a substituted monocyclic heterocyclic group, aromatic group, a substituted aromatic group, a heteroaromatic group, and a substituted heteroaromatic group.

$R^9$ is a hydrogen atom or a lower monovalent hydrocarbon group. Preferably, $R^9$ is a hydrogen atom.

$R^{10}$ is a hydrogen atom or a lower monovalent hydrocarbon group. Preferably, $R^{10}$ is a hydrogen atom.

Component A) may also be any optical isomer, diastereomer, and enantiomer of any of the above structures; or any pharmaceutically-acceptable salts of any of the above structures; or any biohydrolyzable amides, esters, and imides of any of the above structures; or combinations thereof.

The prostaglandin used in this invention preferably has the formula:

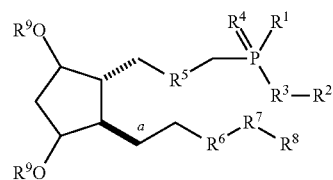

wherein, $R^1$, $R^2$, $R^3$, $R^4$, $R^5$, $R^6$, $R^7$, $R^8$, $R^9$, and bond a are as described above. More preferably, $R^9$ is a hydrogen atom.

Suitable prostaglandins for component A) can be prepared by conventional organic syntheses. Examples of suitable prostaglandins for component A) can be prepared by the following reaction scheme.

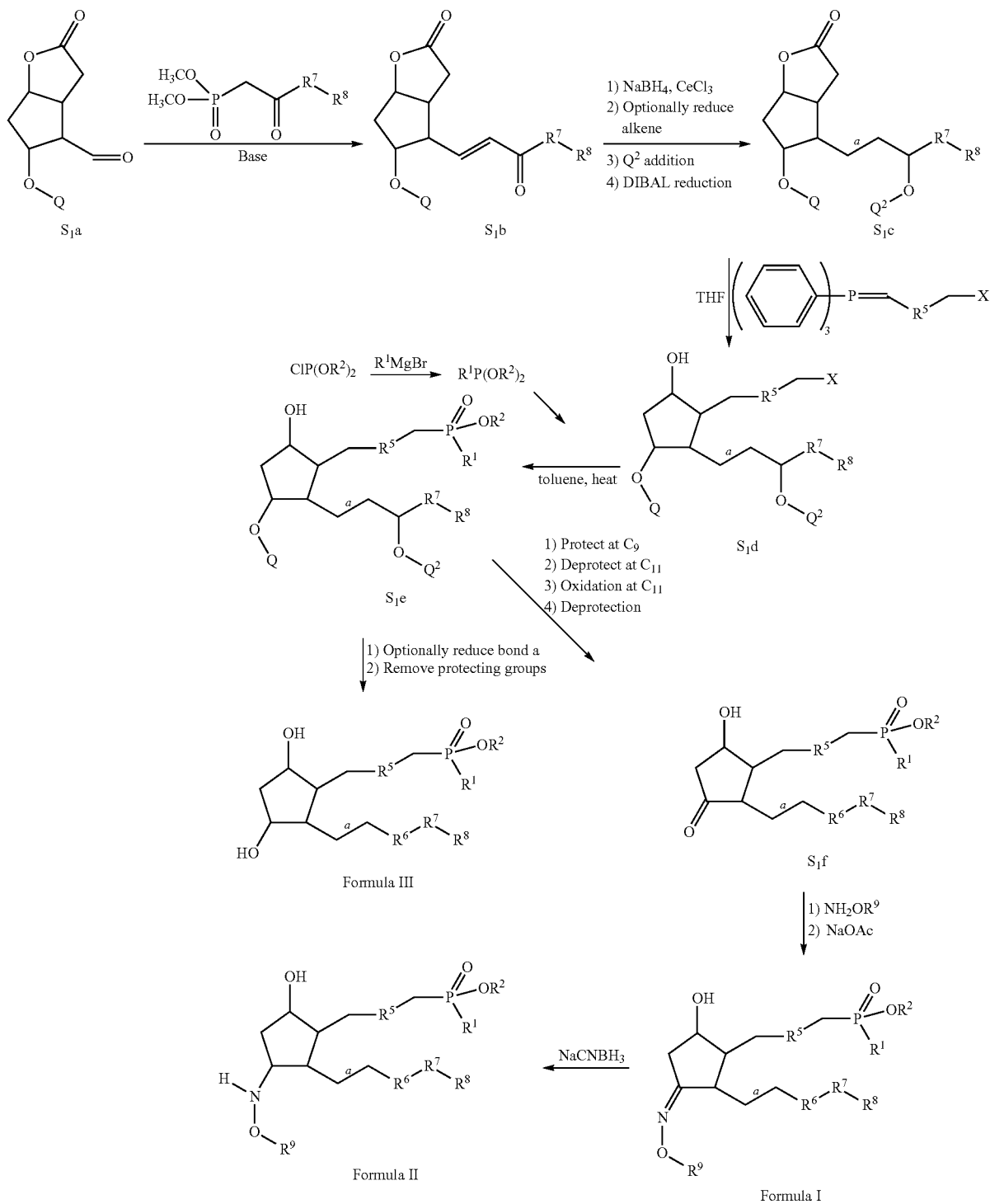

In the reaction scheme above, $R^1$, $R^2$, $R^5$, $R^6$, $R^7$, $R^8$, $R^9$, and bond a are as described above, X is a halogen atom, and Q and $Q^2$ are protecting groups. The Corey Lactone ($S_1a$) starting material is commercially available (from Aldrich Chemical Company or Cayman Chemical Company). Known Wadsworth-Horner-Emmons chemistry is used to attach the bottom chain of the desired prostaglandin to the Corey Lactone, creating compounds of the type $S_1b$. There follows standard prostaglandin omega chain manipulation and functional group protection, including optional alkene reduction, which creates compounds of type $S_1c$. At this point, the standard course of prostaglandin synthesis is altered; the omega-functionalized Wittig reagent depicted is used to create 2-decarboxy prostaglandin derivatives of the type $S_1d$. When the carboxycyclic acid containing prostaglandin is available, compounds of the type $S_1d$ are also obtained by a one-carbon degradation using a modification of the Hunsdiecker reaction.

Compounds depicted by S1e are available from compounds of the type S1d via a phosphinite coupling reaction with an alkyl diethyloxyphosphinite, which is obtained, as shown, from the chlorodiethyloxyphosphine reagent, which is commercially available. Compounds depicted by Formula III are available from compounds of the type S1e via optional removal of the alkene and subsequent removal of the protecting groups Q and $Q^2$ of S1e.

Alternatively, compounds of the type S1f can be prepared from intermediate S1e, where the protecting groups Q and $Q^2$ are judiciously selected from a variety available to those skilled in the art (see, for example: *Protecting Groups in Organic Synthesis* by Greene, T. W. and Wuts, P. G. M., $2^{nd}$ ed., Wiley & Sons, Inc., 1991). Subsequent removal of Q at C11, followed by oxidation would give the ketone precursor to S1f. Compounds of the type S1f can then be obtained by final deprotection.

Compounds of Formula I can be prepared from compounds of formula S1f by condensation with hydroxyl amine. Compounds of Formula II can be reduced to prepare compounds of Formula I by treatment with sodium cyanoborohydride in THF:acetic acid (1:1) and thereafter quenching with HCl. Using conventional organic synthesis techniques, one skilled in the art could prepare prostaglandins suitable for use in this invention.

Examples of suitable prostaglandins of Formula I include Formula 1A. Formula 1A is

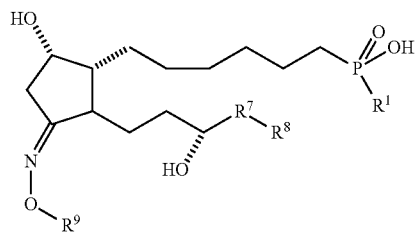

wherein $R^1$, $R^7$, $R^8$, and $R^9$, are defined in Table 1A.

TABLE 1A

| Substituents in Formula 1A | | | |
|---|---|---|---|
| $R^9$ | $R^1$ | $R^7$ | $R^8$ |
| H | $CH_3$ | $CH_2S$ | 3-F-phenyl |
| H | $CH_2CH_3$ | $CH_2S$ | 2-F-phenyl |
| H | $CH_3$ | $CH_2O$ | 3-F-phenyl |
| H | $CH_3$ | $CH_2CH_2CH_2CH_2$ | $CH_3$ |
| H | $CH_3$ | $CH_2CH_2CH_2CH_2CH_2$ | $CH_3$ |
| H | $CH_3$ | $CH_2O$ | 3-Cl-phenyl |
| H | $CH_3$ | $CH_2NH$ | 2,4-diF-phenyl |
| $CH_3$ | $CH_3$ | $CH_2CH_2CH_2CH_2$ | $CH_3$ |
| H | $CH_2CH_3$ | $CH_2S$ | benzothiophen-3-yl |
| H | $CH_2CH_2CH_2CH_3$ | $-C\equiv C-$ | 2-F-phenyl |

Examples of suitable prostaglandins of Formula II include Formula 2A.

Formula 2A is

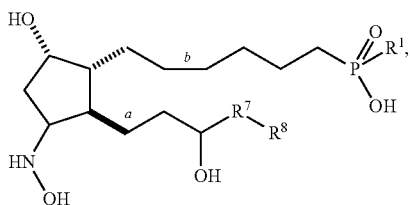

wherein a, b, $R^1$, and $R^7$-$R^8$ are defined in Table 2A.

TABLE 2A

| Substituents in Formula 2A | | | |
|---|---|---|---|
| b | a | $R^1$ | $R^7$—$R^8$ |
| cis | trans | $CH_3$ | phenyl |
| single | single | $CH_3$ | 2-F-phenyl ethynyl |
| single | single | $CH_2CH_3$ | benzothiophen-2-yl |
| single | single | $CH_2CH_3$ | $CH_2NH$-phenyl |

TABLE 2A-continued

| b | a | R¹ | R⁷—R⁸ |
|---|---|---|---|
| cis | trans | $CH_2CH_3$ | 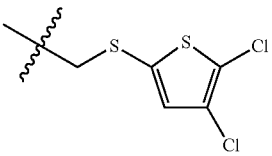 [SMILES: *CSc1cc(Cl)c(Cl)s1] |
| single | single | $CH(CH_3)_2$ | 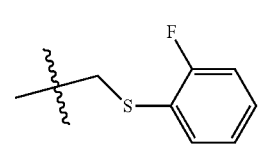 [SMILES: *CSc1ccccc1F] |

Examples of suitable prostaglandins of Formula III include Formulae 3A and 3B.

Formula 3A is

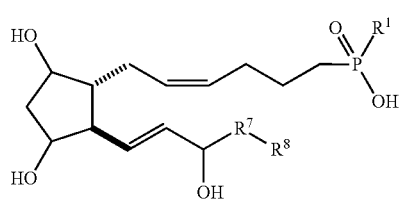

wherein $R^1$, $R^7$, and $R^8$ are defined in Table 3A.

TABLE 3A

| R¹ | R⁷ | R⁸ |
|---|---|---|
| $CH_3$ | $CH_2CH_2$ | 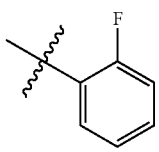 [SMILES: *c1ccccc1F] |
| $CH_3$ | $CH_2S$ | 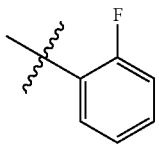 [SMILES: *c1ccccc1F] |
| $CH_3$ | $CH_2O$ | 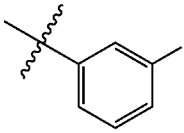 |
| $CH_2CH_3$ | $CH_2O$ | 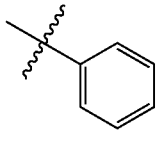 [SMILES: *c1ccccc1] |

TABLE 3A-continued

| R¹ | R⁷ | R⁸ |
|---|---|---|
| $CH_2CH_3$ | $CH_2O$ | 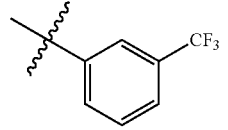 [SMILES: *c1cccc(C(F)(F)F)c1] |
| $CH_2CH_2CH_3$ | $CH_2CH_2$ | 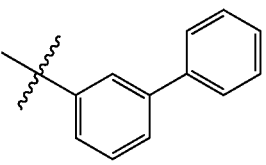 [SMILES: *c1cccc(-c2ccccc2)c1] |
| $CH_3$ | $CH_2NH$ | 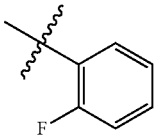 [SMILES: *c1ccccc1F] |
| $CH_3$ | $CH_2NH$ | 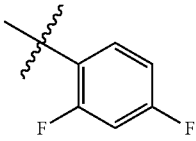 [SMILES: *c1ccc(F)cc1F] |
| $CH_3$ | $CH_2CH_2CH_2CH_2$ | $CH_3$ |
| $CH_2CH_3$ | $CH_2$ | 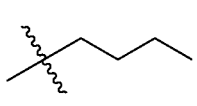 [SMILES: *CCCC] |
| $CH_3$ | $CH_2O$ | 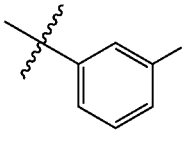 |
| $CH_3$ | $CH_2CH=CHCH_2$ | $CH_3$ |
| $CH_3$ | $CH_2O$ | 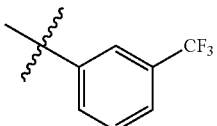 |
| $CH_2CH_2CH_3$ | $CH_2CH_2$ | 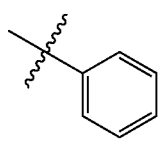 [SMILES: *c1ccccc1] |
| $CH_3$ | $CH_2$ | 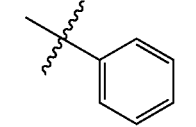 [SMILES: *c1ccccc1] |
| $CH_2CH_3$ | $CH_2O$ | 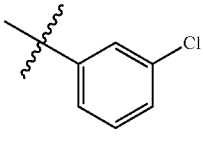 [SMILES: *c1cccc(Cl)c1] |

Formula 3B is

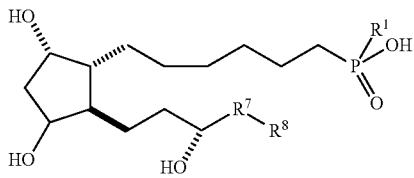

wherein $R^1$, $R^7$, and $R^8$ are defined in Table 3B.

TABLE 3B

| Substituents in Formula 3B | | |
|---|---|---|
| $R^1$ | $R^7$ | $R^8$ |
| $CH_3$ | $CH_2S$ | 2-fluorophenyl |
| $CH_2CH_3$ | CH=CH | phenyl |
| $CH_3$ | C≡C | phenyl |
| $CH_3$ | —CH=C=CH— | phenyl |
| $CH_3$ | $CH_2S$ | phenyl |
| $CH_3$ | $CH_2O$ | 2-fluorophenyl |
| $CH_2CH_3$ | $CH_2O$ | 3-trifluoromethylphenyl |
| $CH_3$ | $CH_2CH_2$ | phenyl |
| $CH_3$ | $CH_2NH$ | phenyl |
| H | $CH_2NH$ | phenyl |

Compositions of the Invention

Hair Loss

This invention further relates to a composition for treating hair loss. "Treating hair loss" means arresting hair loss, reversing hair loss, or both, and promoting hair growth. The composition comprises A) the PGF described above and B) a carrier. The composition may further comprise C) one or more optional activity enhancers.

The composition can be a pharmaceutical or cosmetic composition, administered for treatment or prophylaxis of hair loss. Standard pharmaceutical formulation techniques are used, such as those disclosed in *Remington's Pharmaceutical Sciences*, Mack Publishing Company, Easton, Pa. (1990).

The composition further comprises component B) a carrier. "Carrier" means one or more compatible substances that are suitable for administration to a mammal. Carrier includes solid or liquid diluents, hydrotopes, surface-active agents, and encapsulating substances. "Compatible" means that the components of the composition are capable of being commingled with the prostaglandins, and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both, depending on the intended use as described herein.

The choice of carrier for component B) depends on the route by which A) the prostaglandin will be administered and the form of the composition. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis). Topical administration directly to the locus of desired hair growth is preferred.

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) surfactants, combinations thereof, and others.

Ingredient a) is a diluent. Suitable diluents include sugars such as glucose, lactose, dextrose, and sucrose; polyols such as propylene glycol; calcium carbonate; sodium carbonate; glycerin; mannitol; sorbitol; and maltodextrin.

Ingredient b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*.

Ingredient c) is a binder. Suitable binders include polyvinylpyrrolidone; magnesium aluminum silicate; starches such as corn starch and potato starch; gelatin; tragacanth; and cellulose and its derivatives, such as sodium carboxymethylcellulose, ethylcellulose, methylcellulose, microcrystalline cellulose, and hydroxypropylmethylcellulose; carbomer; providone; acacia; guar gum; and xanthan gum.

Ingredient d) is a disintegrant. Suitable disintegrants include agar, alginic acid and the sodium salt thereof, effervescent mixtures, croscarmelose, crospovidone, sodium carboxymethyl starch, sodium starch glycolate, clays, and ion exchange resins.

Ingredient e) is a colorant such as an FD&C dye.

Ingredient f) is a flavor such as menthol, peppermint, and fruit flavors.

Ingredient g) is a sweetener such as saccharin and aspartame.

Ingredient h) is an antioxidant such as butylated hydroxyanisole, butylated hydroxytoluene, and vitamin E.

Ingredient j) is a preservative such as phenol, alkyl esters of parahydroxybenzoic acid, benzoic acid and the salts thereof, boric acid and the salts thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben, and sodium benzoate.

Ingredient k) is a glidant such as silicon dioxide.

Ingredient m) is a solvent, such as water, isotonic saline, ethyl oleate, alcohols such as ethanol, glycerin, glycols (e.g., polypropylene glycol and polyethylene glycol), and buffer solutions (e.g., phosphate, potassium acetate, boric carbonic, phosphoric, succinic, malic, tartaric, citric, acetic, benzoic, lactic, glyceric, gluconic, glutaric, and glutamic).

Ingredient n) is a suspending agent. Suitable suspending agents include AVICEL® RC-591 from FMC Corporation of Philadelphia, Pa. and sodium alginate.

Ingredient o) is a surfactant such as lecithin, polysorbate 80, sodium lauryl sulfate, polyoxyethylene sorbitan fatty acid esters, polyoxyethylene monoalkyl ethers, sucrose monoesters, lanolin esters, and lanolin ethers. Suitable surfactants are known in the art and commercially available, e.g., the TWEENS® from Atlas Powder Company of Wilmington, Del.

Compositions for parenteral administration typically comprise A) 0.1 to 10% of a prostaglandin and B) 90 to 99.9% of a carrier comprising a) a diluent and m) a solvent. Preferably, component a) is propylene glycol and m) is ethanol or ethyl oleate.

Compositions for oral administration can have various dosage forms. For example, solid forms include tablets, capsules, granules, and bulk powders. These oral dosage forms comprise a safe and effective amount, usually at least 5%, and preferably from 25% to 50%, of A) the prostaglandin. The oral dosage compositions further comprise B) 50 to 95% of a carrier, preferably 50 to 75%.

Tablets can be compressed, tablet triturates, enteric-coated, sugar-coated, film-coated, or multiple-compressed. Tablets typically comprise A) the prostaglandin, and B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose, and sucrose. Preferred binders include starch, and gelatin. Preferred disintegrants include alginic acid, and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin, or f) flavors such as menthol, peppermint, and fruit flavors.

Capsules (including time release and sustained release formulations) typically comprise A) the prostaglandin, and B) a carrier comprising one or more a) diluents disclosed above in a capsule comprising gelatin. Granules typically comprise A) the prostaglandin, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art can optimize appropriate ingredients without undue experimentation.

The solid compositions may also be coated by conventional methods, typically with pH or time-dependent coatings, such that A) the prostaglandin is released in the gastrointestinal tract at various times to extend the desired action. The coatings typically comprise one or more components selected from the group consisting of cellulose acetate phthalate, polyvinylacetate phthalate, hydroxypropyl methyl cellulose phthalate, ethyl cellulose, acrylic resins such as EUDRAGIT® coatings (available from Rohm & Haas G.M.B.H. of Darmstadt, Germany), waxes, shellac, polyvinylpyrrolidone, and other commercially available film-coating preparations such as Dri-Klear, manufactured by Crompton & Knowles Corp., Mahwah, N.J. or OPADRY® manufactured by Colorcon, Inc., of West Point, Pa.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise A) the prostaglandin and B) a carrier comprising ingredients selected from the group consisting of a) diluents, e) colorants, and f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethylcellulose, and hydroxypropylmethylcellulose. Such compositions may further comprise b) lubricants, e) colorants, f) flavors, g) sweeteners, h) antioxidants, and k) glidants.

The compositions for treating hair loss may further comprise component C) an optional activity enhancer. Component C) is preferably selected from the group consisting of i) hair growth stimulants (other than the prostaglandin) and ii) penetration enhancers.

Component i) is an optional hair growth stimulant. Component i) is exemplified by vasodilators, antiandrogens, cyclosporins, cyclosporin analogs, antimicrobials, anti-inflammatories, thyroid hormones, thyroid hormone derivatives, and thyroid hormone analogs, non-selective prostaglandin agonists or antagonists, retinoids, triterpenes, combinations thereof, and others. "Non-selective prostaglandin" agonists and antagonists differ from component A) in that they do not selectively activate the FP receptor, and they may activate other receptors.

Vasodilators such as potassium channel agonists including minoxidil and minoxidil derivatives such as aminexil and those described in U.S. Pat. Nos. 3,382,247, 5,756,092, 5,772,990, 5,760,043, 5,466,694, 5,438,058, 4,973,474, and cromakalin and diazoxide can be used as optional hair growth stimulants in the composition.

Examples of suitable antiandrogens include 5-α-reductase inhibitors such as finasteride and those described in U.S. Pat. No. 5,516,779, and in Nane et al., Cancer Research 58, "Effects of Some Novel Inhibitors of C17,20-Lyase and 5α-Reductase in vitro and in vivo and Their Potential Role in the Treatment of Prostate Cancer," as well as cyproterone acetate, azelaic acid and its derivatives and those compounds described in U.S. Pat. No. 5,480,913, flutamide, and those compounds described in U.S. Pat. Nos. 5,411,981, 5,565,467, and 4,910,226.

Antimicrobials include selenium sulfide, ketoconazole, triclocarbon, triclosan, zinc pyrithione, itraconazole, asiatic acid, hinokitiol, mipirocin and those described in EPA 0,680,745, clinacycin hydrochloride, benzoyl peroxide, benzyl peroxide and minocyclin.

Examples of suitable anti-inflammatories include glucocorticoids such as hydrocortisone, mometasone furoate and prednisolone, nonsteroidal anti-inflammatories including cyclooxygenase or lipoxygenase inhibitors such as those described in U.S. Pat. No. 5,756,092, and benzydamine, salicylic acid, and those compounds described in EPA 0,770,399, published May 2, 1997, WO 94/06434, published Mar. 31, 1994, and FR 2,268,523, published Nov. 21, 1975.

3,5,3'-Triiodothyronine is an example of a suitable thyroid hormone.

Examples of suitable non-selective prostaglandins agonists and antagonists include compounds such as those described in WO 98/33497, Johnstone, published Aug. 6, 1998, WO 95/11003, Stjernschantz, published Apr. 27, 1995, JP 97-100091, Ueno and JP 96-134242, Nakamura.

Suitable retinoids include isotretinoin, acitretin, and tazarotene.

Other optional hair growth stimulants for component i) include benzalkonium chloride, benzethonium chloride, phenol, estradiol, chlorpheniramine maleate, chlorophyllin derivatives, cholesterol, salicylic acid, cysteine, methionine, red pepper tincture, benzyl nicotinate, D,L-menthol, peppermint oil, calcium pantothenate, panthenol, castor oil, prednisolone, resorcinol, chemical activators of protein kinase C, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, flavinoids, ascomycin derivatives and analogs, histamine antagonists such as diphenhydramine hydrochloride, triterpenes such as oleanolic acid and ursolic acid and those described in U.S. Pat. Nos. 5,529,769, 5,468,888, 5,631,282, and 5,679,705, JP 10017431, WO 95/35103, JP 09067253, WO 92/09262, JP 62093215, and JP 08193094; saponins such as those described in EP 0,558,509 to Bonte et al., published Sep. 8, 1993 and WO 97/01346 to Bonte et al., published Jan. 16, 1997, proteoglycanase or glycosaminoglycanase inhibitors such as those described in U.S. Pat. Nos. 5,015,470, 5,300,284, and 5,185,325, estrogen agonists and antagonists, pseudoterins, cytokine and growth factor promoters, analogs or inhibitors such as interleukin1 inhibitors, interleukin-6 inhibitors, interleukin-10 promoters, and tumor necrosis factor inhibitors, vitamins such as vitamin D analogs and parathyroid hormone antagonists, Vitamin B12 analogs and panthenol, interferon agonists and antagonists, hydroxyacids such as those described in U.S. Pat. No. 5,550,158, benzophenones, and hydantoin anticonvulsants such as phenytoin, and combinations thereof.

Other additional hair growth stimulants are described in JP 09-157,139 to Tsuji et al., published Jun. 17, 1997; EP 0277455 A1 to Mirabeau, published Aug. 10, 1988; WO 97/05887 to Cabo Soler et al., published Feb. 20, 1997; WO 92/16186 to Bonte et al., published Mar. 13, 1992; JP 62-93215 to Okazaki et al., published Apr. 28, 1987; U.S. Pat. No. 4,987,150 to Kurono et al., issued Jan. 22, 1991; JP 290811 to Ohba et al., published Oct. 15, 1992; JP 05-286, 835 to Tanaka et al., published Nov. 2, 1993, FR 2,723,313 to Greff, published Aug. 2, 1994, U.S. Pat. No. 5,015,470 to Gibson, issued May 14, 1991, U.S. Pat. No. 5,559,092, issued Sep. 24, 1996, U.S. Pat. No. 5,536,751, issued Jul. 16, 1996, U.S. Pat. No. 5,714,515, issued Feb. 3, 1998, EPA 0,319,991, published Jun. 14, 1989, EPA 0,357,630, published Oct. 6, 1988, EPA 0,573,253, published Dec. 8, 1993, JP 61-260010, published Nov. 18, 1986, U.S. Pat. No. 5,772,990, issued Jun. 30, 1998, U.S. Pat. No. 5,053,410, issued Oct. 1, 1991, and U.S. Pat. No. 4,761,401, issued Aug. 2, 1988.

The most preferred activity enhancers are minoxidil and finasteride, most preferably minoxidil.

Component ii) is a penetration enhancer that can be added to all of the compositions for systemic administration. The amount of component ii), when present in the composition, is typically 1 to 5%. Examples of penetration enhancers include 2-methyl propan-2-ol, propan-2-ol, ethyl-2-hydroxypropanoate, hexan-2,5-diol, polyoxyethylene(2) ethyl ether, di(2-hydroxypropyl) ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethylhexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, omega three fatty acids and fish oils, and combinations thereof.

In a preferred embodiment of the invention, the prostaglandins are topically administered. Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like. Topical compositions comprise: component A) the prostaglandin described above and component B) a carrier. The carrier of the topical composition preferably aids penetration of the prostaglandins into the skin to reach the environment of the hair follicle. Topical compositions preferably further comprise C) one or more of the optional activity enhancers described above.

The exact amounts of each component in the topical composition for treating hair loss depend on various factors. The amount of component A) depends on the $IC_{50}$ of the prostaglandin selected. "$IC_{50}$" means inhibitory concentration $50^{th}$ percentile. The amount of component A) added to the topical composition is:

$$IC_{50} \times 10^{-2} \geq \% \text{ of component A} \geq IC_{50} \times 10^{-3},$$

where $IC_{50}$ is expressed in nanomolar units. For example, if the $IC_{50}$ of the prostaglandin is 1 nM, the amount of component A) will be 0.001 to 0.01%. If the $IC_{50}$ of the prostaglandin is 10 nM, the amount of component A) will be 0.01 to 0.1%. If the $IC_{50}$ of the prostaglandin is 100 nM, the amount of component A) will be 0.1 to 1.0%. If the $IC_{50}$ of the prostaglandin is 1000 nM, the amount of component A) will be 1.0 to 10%, preferably 1.0 to 5%. If the amount of component A) is outside the ranges specified above (i.e., either higher or lower), efficacy of the treatment may be reduced. $IC_{50}$ can be calculated according to the method in Reference Example 1, below. One skilled in the art can calculate $IC_{50}$ without undue experimentation.

The topical composition preferably further comprises 1 to 20% component C), and a sufficient amount of component B) such that the amounts of components A), B), and C), combined equal 100%. The amount of B) the carrier employed in conjunction with the prostaglandin is sufficient to provide a practical quantity of composition for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B) the carrier may comprise a single ingredient or a combination of two or more ingredients. In the topical compositions, component B) is a topical carrier. Preferred topical carriers comprise one or more ingredients selected from the group consisting of water, alcohols, aloe vera gel, allantoin, glycerin, vitamin A and E oils, mineral oil, propylene glycol, polypropylene glycol-2 myristyl propionate, dimethyl isosorbide, combinations thereof, and the like. More preferred carriers include propylene glycol, dimethyl isosorbide, and water.

The topical carrier may comprise one or more ingredients selected from the group consisting of q) emollients, r) propellants, s) solvents, t) humectants, u) thickeners, v) powders, and w) fragrances in addition to, or instead of, the preferred topical carrier ingredients listed above. One skilled in the art would be able to optimize carrier ingredients for the topical compositions without undue experimentation.

Ingredient q) is an emollient. The amount of ingredient q) in the topical composition is typically 5 to 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, polydimethylsiloxane, and combinations thereof. Preferred emollients include stearyl alcohol and polydimethylsiloxane.

Ingredient r) is a propellant. The amount of ingredient r) in the topical composition is typically 5 to 95%. Suitable propellants include propane, butane, isobutane, dimethyl ether, carbon dioxide, nitrous oxide, and combinations thereof.

Ingredient s) is a solvent. The amount of ingredient s) in the topical composition is typically 5 to 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient t) is a humectant. The amount of ingredient t) in the topical composition is typically 5 to 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient u) is a thickener. The amount of ingredient u) in the topical composition is typically 0 to 95%.

Ingredient v) is a powder. The amount of ingredient v) in the topical composition is typically 0 to 95%. Suitable powders include chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically 0.001 to 0.5%, preferably 0.001 to 0.1%.

Component C) the optional activity enhancer is as described above. Any of the i) hair growth stimulants and ii) penetration enhancers may be added to the topical compositions. Preferably, the topical composition comprises 0.01 to 15% of component i) the optional hair growth stimulant. More preferably, the composition comprises 0.1 to 10%, and most preferably 0.5 to 5% of component i). Preferably, the topical composition comprises 1 to 5% of component ii).

In an alternative embodiment of the invention, the topical composition may be applied to growing hair and skin in the locus of the growing hair to darken to darken hair, reverse hair graying, and thicken the hair. For example, the topical composition may be applied to hair growing on the scalp or eyelashes. The topical composition can be, for example, a cosmetic composition prepared as described above. An example of a composition that may be applied to eyelashes is a mascara. The prostaglandin may be added to mascara compositions known in the art, such as the mascara described in U.S. Pat. No. 5,874,072, which is hereby incorporated by reference. The mascara comprises dd) a water-insoluble material, ee) a water-soluble, film-forming polymer, ff) a wax, o) a surfactant, gg) a pigment, and s) a solvent.

Ingredient dd) is a water-insoluble material selected from the group consisting of acrylate copolymers; styrene/acrylate/methacrylate copolymers; acrylic latex; styrene/acrylic ester copolymer latex; polyvinylacetate latex; vinyl acetate/ethylene copolymer latex; styrene/butadiene copolymer latex; polyurethane latex; butadiene/acrylonitrile copolymer latex; styrene/acrylate/acrylonitrile copolymer latex; and mixtures thereof, wherein the acrylate copolymers, and the styrene/acrylate/methacrylate copolymers additionally comprise ammonia, propylene glycol, a preservative and a surfactant.

Ingredient ee) is a water-soluble, film-forming polymer. Ingredient ee) is selected from the group consisting of vinyl alcohol/poly(alkyleneoxy)acrylate, vinyl alcohol/vinyl acetate/poly-(alkyleneoxy)acrylate, polyethylene oxide, polypropylene oxide, acrylates/octyl-acrylamide copolymers and mixtures thereof.

Ingredient ff) is a wax. "Wax" means a lower-melting organic mixture or compound of high molecular weight, solid at room temperature and generally similar in composition to fats and oils except that they contain no glycerides. Some are hydrocarbons, others are esters of fatty acids and alcohols. Waxes useful in this invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55 and 100° C.

Ingredient o) is surfactant, as described above. Ingredient o) in the mascara is preferably a surfactant having an HLB from 3 to 15. Suitable surfactants include those disclosed in the *C.T.F.A. Cosmetic Ingredient Handbook*, pp. 587-592 (1992); *Remington's Pharmaceutical Sciences*, 15th Ed., pp. 335-337 (1975); and *McCutcheon's Volume 1, Emulsifiers & Detergents*, North American Edition, pp. 236-239 (1994).

Ingredient gg) is a pigment. Suitable pigments include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), and the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Ingredient s) is a solvent described above, preferably water.

The amount of A) the prostaglandin added to the mascara is as described above for topical compositions.

The prostaglandins may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds uses liposomes as described in Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404-407 (1993); Wallach and Philippot, "New Type of Lipid Vesicle: Novasome®", *Liposome Technology*, Vol. 1, pp. 141-156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The prostaglandins may also be administered by iontophoresis. See, e.g., Internet site www.unipr.it/arpa/dipfarm/erasmus/erasm14.html; Banga et al., "Hydrogel-based Iontotherapeutic Delivery Devices for Transdermal Delivery of Peptide/Protein Drugs", *Pharm. Res.*, Vol. 10 (5), pp. 697-702 (1993); Ferry, "Theoretical Model of Iontophoresis Utilized in Transdermal Drug Delivery", *Pharmaceutical Acta Helvetiae*, Vol 70, pp. 279-287 (1995); Gangarosa et al., "Modern Iontophoresis for Local Drug Delivery", *Int. J. Pharm.*, Vol. 123, pp. 159-171 (1995); Green et al., "Iontophoretic Delivery of a Series of Tripeptides Across the Skin in vitro", *Pharm. Res.*, Vol 8, pp. 1121-1127 (1991); Jadoul et al., "Quantification and Localization of Fentanyl and TRH Delivered by Iontophoresis in the Skin", *Int. J. Pharm.*, Vol. 120, pp. 221-8 (1995); O'Brien et al., "An Updated Review of its Antiviral Activity, Pharmacokinetic Properties and Therapeutic Efficacy", *Drugs*, Vol. 37, pp. 233-309 (1989); Parry et al., "Acyclovir Biovailability in Human Skin", *J. Invest. Dermatol.*, Vol. 98 (6), pp. 856-63 (1992); Santi et al., "Drug Reservoir Composition and Transport of Salmon Calcitonin in Transdermal Iontophoresis", *Pharm. Res.*, Vol 14 (1), pp. 63-66 (1997); Santi et al., "Reverse Iontophoresis—Parameters Determining Electroosmotic Flow: I. pH and Ionic Strength", *J. Control. Release*, Vol. 38, pp. 159-165 (1996); Santi et al., "Reverse Iontophoresis—Parameters Determining Electroosmotic Flow: II. Electrode Chamber Formulation", *J. Control. Release*, Vol. 42, pp. 29-36 (1996); Rao et al., "Reverse Iontophoresis: Noninvasive Glucose Monitoring in vivo in Humans", *Pharm. Res.*, Vol. 12 (12), pp. 1869-1873 (1995); Thysman et al., "Human Calcitonin Delivery in Rats by Iontophoresis", J. Pharm. Pharmacol., Vol. 46, pp. 725-730 (1994); and Volpato et al., "Iontophoresis Enhances the Transport of Acyclovir through Nude Mouse Skin by Electrorepulsion and Electroosmosis", *Pharm. Res.*, Vol. 12 (11), pp. 1623-1627 (1995).

The prostaglandins may be included in kits comprising a prostaglandin, a systemic or topical composition described above, or both; and information, instructions, or both that use of the kit will provide treatment for hair loss in mammals (particularly humans). The information and instructions may be in the form of words, pictures, or both, and the like. In addition or in the alternative, the kit may comprise a prostaglandin, a composition, or both; and information, instructions, or both, regarding methods of application of the prostaglandin or composition, preferably with the benefit of treating hair loss in mammals.

Bone Disorders

In addition to benefits in treating hair loss, the prostaglandins of this invention may also be useful to treat bone disorders. Without wishing to be bound by theory, it is believed that the prostaglandins are useful in increasing bone volume and trabecular number through formation of new trabeculae, formation of bone mass while maintaining a normalized bone turnover rate, and formation at the endosteal surface without removing bone from the existing cortex.

This invention further relates to compositions for treating bone disorders. Compositions for treating bone disorders can be prepared by standard pharmaceutical formulation techniques, such as those disclosed in *Remington's Pharmaceutical Sciences*, Mack Publishing Company, Easton, Pa. (1990), using the ingredients described above. The preferred routes of administration for treating bone disorders are transdermal, intranasal, rectal, sublingual, and oral.

Suitable oral compositions for treating bone disorders typically comprise A) a prostaglandin described above and B) a carrier. A typical tablet composition comprises A) the prostaglandin and B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose, and sucrose. Preferred lubricants include magnesium stearate, stearic acid, and talc. Preferred binders include microcrystalline cellulose, starch, and gelatin. Preferred disintegrants include sodium starch glycolate, alginic acid, and croscarmelose.

Typical parenteral pharmaceutical compositions for treating bone disorders comprise A) the prostaglandin and B) a carrier comprising ingredients selected from the group consisting of j) preservatives and m) solvents. Preferred preservatives include methyl paraben and ethyl paraben. Preferred solvents include isotonic saline. One skilled in the art can optimize ingredients for the compositions to treat bone disorders without undue experimentation.

The prostaglandins can optionally be used in combination with other ingredients which have a beneficial effect on bone loss. Thus, other actives such as vitamin D analogs, hormones, calcium supplements, diphosphonate compounds such as those extensively described in the literature of the Procter & Gamble Company, combinations thereof, and the like may also be administered to patients in need of such treatment in conjunction with the prostaglandins. Dosage levels and means of administration include pulsed-dosing, and are as described in the literature.

Intraocular Pressure

The prostaglandins used in this invention are also useful in decreasing intraocular pressure. Thus, these prostaglandins are useful in the treatment of glaucoma. This invention further relates to compositions for lowering intraocular pressure. The preferred route of administration for lowering intraocular pressure is topical. Topical pharmaceutical compositions for ocular administration typically comprise A) a prostaglandin, B) a carrier, such as purified water, and one or more ingredients selected from the group consisting of y) sugars such as dextrans, particularly dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethyl cellulose, ethyl cellulose, methyl cellulose, and hydroxypropylmethylcellulose. Hydroxypropylmethylcellulose is preferred.

Examples of aa) salts suitable for use in the for use in the topical pharmaceutical composition for ocular administration include sodium chloride, potassium chloride, and combinations thereof.

Examples of cc) pH adjusting additives include HCl or NaOH in amounts sufficient to adjust the pH of the topical pharmaceutical composition for ocular administration to 7.2-7.5.

Methods of the Invention

Hair Loss

This invention further relates to a method for treating hair loss in mammals. The method comprises administering to a mammal (preferably a human) suffering from hair loss, a prostaglandin described above. For example, a mammal diagnosed with alopecia including male pattern baldness and female pattern baldness can be treated by the methods of this invention. Preferably, a systemic or topical composition comprising A) the prostaglandin and B) a carrier is administered to the mammal. More preferably, the composition is a topical composition comprising A) the prostaglandin, B) the carrier, and C) an optional activity enhancer.

The dosage of the prostaglandin administered to treat hair loss depends on the method of administration. For systemic administration, (e.g., oral, rectal, nasal, sublingual, buccal, or parenteral), typically, 0.5 mg to 300 mg, preferably 0.5 mg to 100 mg, more preferably 0.1 mg to 10 mg, of a prostaglandin described above is administered per day. These dosage ranges are merely exemplary, and daily administration can be adjusted depending on various factors. The specific dosage of the prostaglandin to be administered, as well as the duration of treatment, and whether the treatment is topical or systemic are interdependent. The dosage and treatment regimen will also depend upon such factors as the specific prostaglandin used, the treatment indication, the efficacy of the compound, the personal attributes of the subject (such as, for example, weight, age, sex, and medical condition of the subject), compliance with the treatment regimen, and the presence and seventy of any side effects of the treatment.

For topical administration (e.g., local application on the skin, liposome delivery systems, or iontophoresis), the topical composition is typically administered once per day. The topical compositions are administered daily for a relatively short amount of time (i.e., on the order of weeks). Generally, 6 to 12 weeks is sufficient. The topical compositions are preferably leave-on compositions. In general, the topical composition should not be removed for at least several hours after administration.

In addition to the benefits in treating hair loss, the inventors have found that the prostaglandins in the compositions and methods of this invention also darken and thicken hair and may reverse hair graying. This invention further relates to a method for darkening hair, thickening hair, and reversing hair graying. The method comprises applying the topical composition for treating hair loss to hair, to skin in the locus of hair, or both. In a preferred embodiment of the invention, the topical composition, such as the mascara composition described above, is applied to eyelashes.

Bone Disorders

This invention further relates to methods for treating bone disorders using the prostaglandins described above. The method comprises administering to a mammal (preferably a human) suffering from a bone disorder, a prostaglandin described above. For example, a mammal diagnosed with osteoporosis can be treated by the methods of this invention. Preferably, a systemic composition comprising A) the prostaglandin and B) a carrier is administered to the mammal. The preferred routes of administration for treating bone disorders are transdermal, intranasal, rectal, sublingual, and oral.

The dosage range of the prostaglandin for systemic administration to treat bone disorders is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

Intraocular Pressure

The prostaglandins of the present invention are also useful in decreasing intraocular pressure. Thus, these prostaglandins are useful in the treatment of glaucoma. This invention further relates to a method for lowering intraocular pressure in mammals. The method comprises administering to a mammal (preferably a human) a prostaglandin described above. For example, a mammal diagnosed with glaucoma can be treated by the methods of this invention. The preferred route of administration for treating glaucoma is topical. Preferably, a topical composition for ocular administration described above is administered to the mammal. The topical composition for ocular administration is typically administered once per day. The topical compositions are administered daily for a relatively short amount of time (i.e., on the order of weeks). Generally, 6 to 12 weeks is sufficient.

EXAMPLES

These examples are intended to illustrate the invention to those skilled in the art and should not be interpreted as limiting the scope of the invention set forth in the claims.

Reference Example 1—Radioligand Binding Assay $IC_{50}$ of a prostaglandin can be determined relative to $PGF_{2\alpha}$ using the Radioligand Binding Assay. As a control, the $IC_{50}$ for $PGF_{2\alpha}$ itself should be no lower than 1.0 nM and no higher than 5.0 nM.

In this assay, COS-7 cells are transiently transfected with the hFP recombinant plasmid using LipofectAMINE Reagent. Forty-eight hours later, the tranfected cells are washed with Hank's Balanced Salt Solution (HBSS, without $CaCl_2$, $MgCl_2$, $MgSO_4$, or phenol red). The cells are detached with versene, and HBSS is added. The mixture is centrifuged at 200 g for 10 minutes, at 4° C. to pellet the cells. The pellet is resuspended in Phosphate-Buffered Saline-EDTA buffer (PBS; 1 mM EDTA; pH 7.4; 4° C.). The cells are disrupted by nitrogen cavitation (Parr model 4639), at 800 psi, for 15 minutes at 4° C. The mixture is centrifuged at 1000 g for 10 minutes at 4° C. The supernatant is centrifuged at 100,000 g for 60 minutes at 4° C. The pellet is resuspended to 1 mg protein/mL TME buffer (50 mM Tris; 10 mM $MgCl2$; 1 mM EDTA; pH 6.0; 4° C.) based on protein levels measured using the Pierce BCA Protein Assay kit. The homogenate is mixed for 10 seconds using a Kinematica POLYTRON® (available from KINEMATICA AG, Luzernerstrasse147A CH-6014 Littau, Switzerland). The membrane preparations are then stored at −80° C., until thawed for assay use.

The receptor competition binding assays are developed in a 96 well format. Each well contains 100 g of hFP membrane, 5 nM (3H) $PGF2\alpha$, and the various competing compounds in a total volume of 200 L. The plates are incubated at 23° C. for 1 hour. The incubation is terminated by rapid filtration using the Packard Filtermate 196 harvester through Packard UNIFILTER® GF/B filters (available from Packard Instrument Co., Inc. of Downers Grove Ill.) prewetted with TME buffer. The filter is washed four times with TME buffer. Packard Microscint 20, a high efficiency liquid scintillation cocktail, is added to the filter plate wells and the plates remain at room temperature for three hours prior to counting. The plates are read on a Packard TOPCOUNT® Microplate Scintillation Counter (also available from Packard Instrument Co., Inc.)

Reference Example 2—Telogen Conversion Assay

Prostaglandins are tested for their potential to grow hair using the Telogen Conversion Assay. The Telogen Conversion Assay measures the potential of a prostaglandin to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein is used to screen prostaglandins for potential hair growth by measuring melanogenesis.

Three groups of 44 day-old C3H mice are used: a vehicle control group, a positive control group, and a test prostaglandin group, wherein the test prostaglandin group is administered a prostaglandin used in the method of this invention. The length of the assay is 24 days with 15 treatment days (wherein the treatment days occur Mondays through Fridays). Day 1 is the first day of treatment. A typical study design is shown in Table 4 below. Typical dosage concentrations are set forth in Table 3, however the skilled artisan will readily understand that such concentrations may be modified.

TABLE 4

Assay Parameters

| Group # | Animal # | Compound | Concentration | Application volume | Length of Study |
|---|---|---|---|---|---|
| 1 | 1-10 | Test Compound | 0.01% in vehicle** | 400 µL topical | 26 days |
| 2 | 11-20 | Positive Control (T3)* | 0.01% in vehicle** | 400 µL topical | 26 days |
| 3 | 21-30 | Vehicle** | N/A | 400 µL topical | 26 days |

*T3 is 3,5,3'-triiodothyronine.
**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 5, the grades 0 to 4 represent the following visual observations as the skin progresses from white to bluish-black.

TABLE 5

Evaluation Criteria

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Reference Example 3—Ovariectomized Rat Assay

Bone activity of the prostaglandins can be conveniently demonstrated using an assay designed to test the ability of the prostaglandins to increase bone volume, mass, or density. An example of such assays is the ovariectomized rat assay.

In the ovariectomized rat assay, six-month old rats are ovariectomized, aged 2 months, and then dosed once a day subcutaneously with a prostaglandin. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Reference Example 4—Pharmacological Activity for Glaucoma Assay

Pharmacological activity for glaucoma can be demonstrated using assays designed to test the ability of the subject compounds to decrease intraocular pressure. Examples of such assays are described in the following reference, incorporated herein: C. Iiljebris, G. Selen, B. Resul, J. Sternschantz, and U. Hacksell, "Derivatives of 17-Phenyl-18,19,20-trinorprostaglandin F$_2\alpha$ Isopropyl Ester: Potential Antiglaucoma Agents", *Journal of Medicinal Chemistry*, Vol. 38 No. 2 (1995), pp. 289-304.

Example 1

Compositions for topical administration are made, comprising:

| Component | 1-1 | 1-2 |
|---|---|---|
| Prostaglandin (wt %) | 0.42 | 1.14 |
| IC$_{50}$ the PGF (nM) | 42 | 114 |
| Ethanol (wt %) | 59.74 | 59.32 |
| Propylene Glycol (wt %) | 19.92 | 19.77 |
| Dimethyl Isosorbide (wt %) | 19.92 | 19.77 |

The prostaglandins in the topical compositions are as follows:

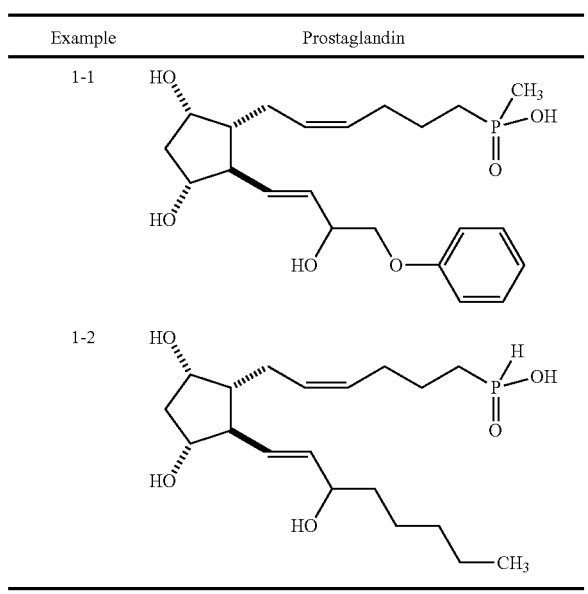

A human male subject suffering from male pattern baldness is treated by a method of this invention. Specifically, for 6 weeks, one of the above compositions is daily administered topically to the subject to induce hair growth.

Example 2

A composition for topical administration is made according to the method of Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404-407 (1993), using a PGF in lieu of cyclosporin A and using the NOVASOME® 1 (available from Micro-Pak, Inc. of Wilmington, Del.) for the non-ionic liposomal formulation.

A human male subject suffering from male pattern baldness is treated each day with the above composition. Specifically, for 6 weeks, the above composition is administered topically to the subject.

Example 3

Shampoos are made, comprising:

| Component | Ex. 3-1 | Ex. 3-2 | Ex. 3-3 | Ex. 3-4 |
|---|---|---|---|---|
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| PGF having $IC_{50}$ of 42 nM | — | 0.42% | 0.42% | — |
| PGF having $IC_{50}$ of 114 nM | 0.11% | — | — | 0.11% |
| Minoxidil | — | — | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

The prostaglandins are the same as in Example 1.

A human subject suffering from male pattern baldness is treated by a method of this invention. Specifically, for 12 weeks, a shampoo described above is used daily by the subject.

Example 4

A mascara composition is prepared. The composition comprises:

| Component | % W/W |
|---|---|
| WATER, DEIONIZED, USP | q.s. |
| BLACK 1080 MICRONIZED TYPE | 10.000 |
| GLYCERYL MONOSTEARATE (2400 TYPE) | 8.500 |
| C18-36 ACID TRIGLYCERIDE | 5.500 |
| STEARIC ACID, TRIPLE PRESSED, LIQUID | 4.000 |
| ETHYL ALCOHOL SD 40-B, 190 PROOF/SERIAL #: | 4.000 |
| BEESWAX WHITE, FLAKES | 3.250 |
| SHELLAC, NF | 3.000 |
| LECITHIN, GRANULAR (TYPE 6450) | 2.500 |
| TRIETHANOLAMINE 99% - TANK | 2.470 |
| PARAFFIN WAX | 2.250 |
| PARAFFIN WAX 118/125 | 2.250 |
| CARNAUBA WAX, NF | 2.000 |
| POTASSIUM CETYL PHOSPHATE | 1.000 |
| PHENOXYETHANOL | 0.800 |
| OLEIC ACID NF | 0.750 |
| DL-PANTHENOL | 0.350 |
| PVP/VA COPOLYMER | 0.250 |
| METHYLPARABEN, NF | 0.200 |
| DIAZOLIDINYL UREA | 0.200 |
| SIMETHICONE | 0.200 |
| ETHYLPARABEN NF | 0.150 |
| PENTAERYTHRITYL HYDROGENATED ROSINATE | 0.150 |
| PROPYLPARABEN, NF | 0.100 |
| TRISODIUM EDTA | 0.100 |
| PROSTAGLANDIN having $IC_{50}$ of 114 nM | 0.114 |

The prostaglandin is the same as in Example 1-2.

A human female subject applies the composition each day. Specifically, for 6 weeks, the above composition is administered topically to the subject to darken and thicken eyelashes.

Example 5

A pharmaceutical composition in the form of a tablet is prepared by conventional methods, such as mixing and direct compaction, formulated as follows:

| Ingredient | Quantity (mg per tablet) |
|---|---|
| Prostaglandin | 5 |
| Microcrystalline Cellulose | 100 |
| Sodium Starch Glycollate | 30 |
| Magnesium Stearate | 3 |

The prostaglandin is the same as in Example 1-2.

When administered orally once daily, the above composition substantially increases bone volume in a patient suffering from osteoporosis.

Example 6

A pharmaceutical compositions in liquid form is prepared by conventional methods, formulated as follows:

| Ingredient | Quantity |
|---|---|
| Prostaglandin | 1 mg |
| Phosphate buffered physiological saline | 10 ml |
| Methyl Paraben | 0.05 ml |

The prostaglandin used is the same as in Example 1-2.

When 1.0 ml of the above composition is administered subcutaneously once daily, the above composition substantially increases bone volume in a patient suffering from osteoporosis.

Example 7

A topical pharmaceutical composition for lowering intraocular pressure are prepared by conventional methods and formulated as follows:

| Ingredient | Amount (wt %) |
|---|---|
| Prostaglandin | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCl and/or NaOH | pH 7.2-7.5 |
| Purified water | q.s. to 100% |

The prostaglandin is the same as in Example 1-2.

When the above composition is administered once daily for 6 to 12 weeks, it lowers intraocular pressure in a patient suffering from glaucoma.

Effects of the Invention

The compositions and methods herein provide a cosmetic benefit with respect to hair growth and appearance in subjects desiring such treatment. The compositions and methods herein also provide pharmaceutical benefits with respect to treating bone disorders and lowering intraocular pressure in subjects needing such treatment.

What is claimed is:

1. A method for darkening and thickening hair comprising applying to growing hair and skin, a composition comprising:
    A) an active ingredient selected from the group consisting of 2-decarboxy-2-phosphinico derivatives of prostaglandins; optical isomers, diastereomers, and enantiomers of the 2-decarboxy-2-phosphinico derivatives; pharmaceutically-acceptable salts of the 2-decarboxy-2-phosphinico derivatives; amides, esters, and imides of the 2-decarboxy-2-phosphinico derivatives; and combinations thereof,
    wherein the 2-decarboxy-2-phosphinico derivative has a structure selected from the group consisting of:

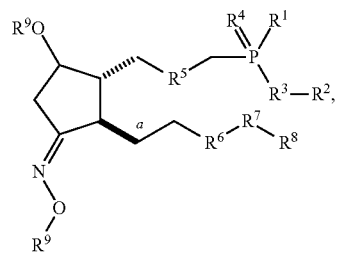
Formula I

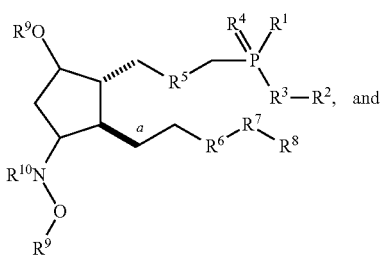
Formula II

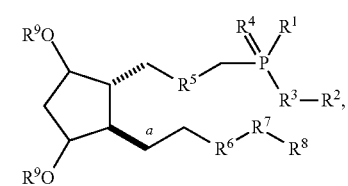
Formula III wherein $R^1$ is selected from the group consisting of a hydrogen atom, and lower monovalent hydrocarbon groups, and lower heterogeneous groups;
$R^2$ is selected from the group consisting of a hydrogen atom, a monovalent hydrocarbon group, a substituted monovalent hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group;
$R^3$ is selected from the group consisting of an oxygen atom, a sulfur atom, and NH;
$R^4$ is selected from the group consisting of an oxygen atom and a sulfur atom;
$R^5$ is a divalent group selected from the group consisting of a hydrocarbon group, a substituted hydrocarbon group, a heterogeneous group, and a substituted heterogeneous group; with the proviso that when $R^5$ is a heterogeneous group, $R^5$ has only one heteroatom, which is selected from the group consisting of oxygen, sulfur, and nitrogen;
bond a is selected from the group consisting of a single bond, a trans double bond, and a triple bond;
$R^6$ is a divalent group selected from the group consisting of —C(O)— and —C($R^9$)(O$R^9$)—;
$R^7$ is selected from the group consisting of a divalent group having the formula —(C$R^9$($R^9$))$_p$—X—(C$R^9$($R^9$))$_q$, wherein p is an integer from 0 to 3 and q is an integer from 0 to 3, and wherein X is selected from the group consisting of an oxygen atom, a divalent hydrocarbon group, a sulfur atom, SO, SO$_2$, and N$R^9$;
$R^8$ is selected from the group consisting of a methyl group, a carbocyclic group, a substituted carbocyclic group, a heterocyclic group, a substituted heterocyclic group, aromatic group, a substituted aromatic group, a heteroaromatic group, a substituted heteroaromatic group;
$R^9$ is selected from the group consisting of a hydrogen atom and a lower monovalent hydrocarbon group; and
$R^{10}$ is selected from the group consisting of a hydrogen atom and a lower monovalent hydrocarbon group.

2. The method of claim 1, wherein the composition is administered by a route selected from the group consisting of systemic and topical routes.

3. The method of claim 2, wherein the composition is a topical composition in a form selected from the group consisting of solutions, oils, creams, ointments, gels, lotions, shampoos, leave-on and rinse-out hair conditioners, milks, cleansers, moisturizers, sprays, and skin patches.

4. The method of claim 3, wherein the composition is a topical composition further comprising B) a topical carrier, wherein the topical carrier comprises an ingredient selected from the group consisting of q) emollients, r) propellants, s) solvents, t) humectants, u) thickeners, v) powders, w) fragrances, water, alcohols, aloe vera gel, allantoin, glycerin, vitamin A and E oils, mineral oil, propylene glycol, dimethyl isosorbide, polypropylene glycol-2 myristyl propionate, and combinations thereof.

5. The method of claim 1, wherein the composition further comprises C) an activity enhancer selected from the group consisting of i) a hair growth stimulant, ii) a penetration enhancer, and combinations thereof.

6. The method of claim 5, wherein component i) is selected from the group vasodilator, an antiandrogen, a cyclosporin, a cyclosporin analog, an antimicrobial, an anti-inflammatory, a thyroid hormone, a thyroid hormone derivative, and a thyroid hormone analog, a non-selective prostaglandin agonist, a non-selective prostaglandin antagonist, a retinoid, a triterpene, and combinations thereof.

7. The method of claim 5, wherein component ii) is selected from the group consisting of 2-methyl propan-2-ol, propan-2-ol, ethyl-2-hydroxypropanoate, hexan-2,5-diol, polyoxyethylene(2) ethyl ether, di(2-hydroxypropyl) ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2hydroxyoctanoic acid, dimethyl sulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, and combinations thereof.

8. The method of claim 2, wherein the composition is a topical composition locally administered on the skin once per day.

9. The method of claim 8, wherein the composition is administered once per day for 6 to 12 weeks.

10. The method of claim 1, wherein $R^2$ is selected from the group consisting of H, $CH_2CO_2H$, $CH_2C(O)NHOH$, methyl, $CF_3$, ethyl, n-propyl, isopropyl, $CH_2CH_2OH$, $CH_2CH(OH)CH_2OH$, benzyl, and t-butyl.

11. The method of claim 1, wherein $R^3$ is selected from the group consisting of an oxygen atom and NH.

12. The method of claim 1, wherein $R^4$ is an oxygen atom.

13. The method of claim 1, wherein $R^5$ has 1 to 5 member atoms.

14. The method of claim 1, wherein $R^6$ is —C(H)(OH)—.

15. The method of claim 1, wherein X is selected from the group consisting of an oxygen atom, a sulfur atom, and $NR^9$.

16. The method of claim 1, wherein $R^8$ is selected from the group consisting of a monocyclic carbocyclic group, a substituted monocyclic carbocyclic group, a monocyclic heterocyclic group, a substituted monocyclic heterocyclic group, aromatic group, a substituted aromatic group, a heteroaromatic group, and a substituted heteroaromatic group.

17. The method of claim 1, wherein $R^9$ is a hydrogen atom.

* * * * *